United States Patent [19]

Ichinose et al.

[11] Patent Number: 4,971,739
[45] Date of Patent: Nov. 20, 1990

[54] METHOD OF PRODUCING FLUORAPATITE AND A MOISTURE SENSITIVE RESISTOR USING FLUORAPATITE OBTAINED BY THE SAME

[75] Inventors: Noboru Ichinose, Yokohama; Hirohumi Tanaka, Anan, both of Japan

[73] Assignee: Nichia Kagaku Kogyo K.K., Japan

[21] Appl. No.: 336,911

[22] Filed: Apr. 12, 1989

Related U.S. Application Data

[62] Division of Ser. No. 189,812, Apr. 12, 1988, Pat. No. 4,855,118.

[30] Foreign Application Priority Data

Apr. 15, 1987 [JP] Japan ................................ 62-90935
Apr. 15, 1987 [JP] Japan ................................ 62-90936

[51] Int. Cl.$^5$ .......................... C04B 33/34; H01B 1/06; H01C 3/04
[52] U.S. Cl. ..................................... 264/61; 264/66; 264/67; 252/518; 252/520; 252/521; 338/20; 338/35; 423/301
[58] Field of Search ............... 423/305, 307, 311, 301; 252/518, 521, 520; 338/20, 25, 35; 264/66, 67, 61; 419/38, 45, 10, 20-23

[56] References Cited

U.S. PATENT DOCUMENTS 2,553,595  5/1951  Maier .................................. 423/307
4,157,378  6/1979  Tomlinson et al. ................. 423/308

*Primary Examiner*—Josephine Barr
*Attorney, Agent, or Firm*—Nixon & Vanderhye

[57] ABSTRACT

A method of producing fluorapatite wherein predetermined amounts of calcium monohydrogen phosphate, calcium carbonate, and calcium fluoride are weighed, subjected to a mechanochemical action, and caused to react with one another in water. With this method, a fluorapatite having a uniform composition can be obtained without the accompaniment of by-products. A moisture sensitive resistor of the present invention can be obtained by sintering the fluorapatite produced in accordance with this method. This moisture sensitive resistor has a sufficiently low resistance corresponding to a humidity, and has substantially no hysteresis.

4 Claims, 4 Drawing Sheets

METHOD OF PRODUCING FLUORAPATITE AND A MOISTURE SENSITIVE RESISTOR USING FLUORAPATITE OBTAINED BY THE SAME

This is a division of application Ser. No. 180,812, filed Apr. 12, 1988, now U.S. Pat. No. 4,855,118.

BACKGROUND OF THE INVENTION

1. Field of the Invention

The present invention relates to a method of producing fluorapatite and a moisture sensitive resistor made of sintered body of the fluorapatite obtained by the same.

2. Description of the Prior Art

Fluorapatite [$Ca_{10}(PO_4)_6F_2$; to be described as FAp hereinafter] is a main mineral constituting rock phosphate and used as a phosphor material.

FAp synthesizing methods are roughly classified into a dry method and a wet method.

The dry method includes a step of sintering the raw materials (calcium phosphate and calcium fluoride; calcium pyrophosphate and calcium fluoride; and the like) of FAp at a temperature as high as several hundreds of degrees of centigrade. Therefore, fluorine tends to evaporate easily, and it is difficult to obtain an FAp powder having a uniform composition.

As the wet method, a method involving adding calcium fluoride to a suspension of calcium monohydrogen phosphate and causing the two materials to react to each other, a method hydrolyzing calcium monofluorophosphate dihydrate, and the like are known. However, these methods often accompany by-products. Therefore, it is difficult to obtain pure FAp with these methods.

It is also known as another method of obtaining FAp that, in the process of producing hydroxyapatite, fluorine ions mixed with materials of hydroxyapatite. However, FAp obtained with this method is amorphous.

As still another method of obtaining FAp, a method of mixing calcium fluoride and o-calcium phosphate at a molar ratio of 1:3 and grinding the two materials is known (*Kogyo Kagaku Zasshi*, Vol. 71, No 9, (1968) p. 1307). However, with this method, the starting materials remain unreacted even after grinding for 8 hours, and it is difficult to cause the starting materials to completely react to each other.

The present invention also relates to a moisture sensitive resistor. A moisture sensitive resistor exhibits a resistance corresponding to the relative humidity of the atmosphere.

Moisture sensitive resistors using ceramics or polymer films are known. However, the electric resistance of a moisture sensitive resistor of this type corresponding to the humidity is high. Particularly, under a low humidity conduction, the electric resistance exceeds the upper limit of the practical measurement range (10M$\Omega$ or less) or the sensitivity tends to be poor even when it falls within this range. There are not many moisture sensitive resistors that can measure a resistance at a high precision in a low humidity range.

Moisture sensitive resistors using apatite are also known. Japanese Patent Publication No. 60-35802 discloses a moisture sensitive resistor using FAp, and Japanese Patent Disclosure (Kokai) Nos. 59-60348 and 59-60350 disclose moisture sensitive resistors using hydroxyapatite. However, the resistances of these resistors corresponding to the humidity are also high. In an attempt to decrease the resistance, some of the cations of apatites has been substituted by other cations (e.g., Li, Na, K, Ag, and Cu). However, even after substitution, the resistances of these resistors are not sufficiently low. In sintered hydroxyapatite, a hysteresis occurs in the resistance when measurement is performed from high to low humidity side and vice versa, resulting in low reliability.

SUMMARY OF THE INVENTION

It is, therefore, an object of the present invention to provide a method of producing FAp having a uniform composition without substantially accompanying by-products.

In order to achieve this object, according to the present invention, a mixture containing calcium monohydrogen phosphate, calcium carbonate, and calcium fluoride at a predetermined ratio is subjected to a mechanochemical action, and is thereafter reacted to each other in water.

It is another object of the present invention to provide a moisture sensitive resistor wherein a resistance corresponding to a humidity is sufficiently low and a hysteresis does not substantially occur. In order to achieve this object, in the present invention, FAp obtained by the above producing method is sintered and then used as the moisture sensitive resistor.

DETAILED DESCRIPTION OF THE PREFERRED EMBODIMENTS

Figure 1:
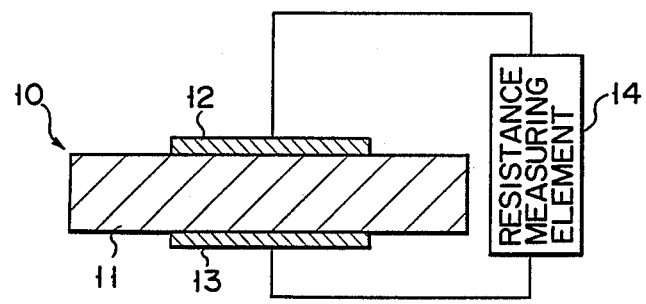
FIG. 1 is a sectional view of a moisture sensitive element having a moisture sensitive resistor according to the present invention.

In the FAp producing method of the present invention, calcium monohydrogen phosphate ($CaHPO_4$), calcium carbonate ($CaCO_3$), and calcium fluoride ($CaF_2$) are used as the raw materials. These materials are mixed at a predetermined ratio, or a substantially stoichiometric ratio (i.e., $CaHPO_4:CaCO_3:CaF_2=6:3:1$), and are subjected to a mechanochemical action. Then, these materials are caused to react with one another in water (solid-water system reaction).

A mechanochemical action is what a solid material performs to have its physicochemical property changed by using part of the mechanical energy it has received (*Kogyo Kagaku Zasshi* Vol. 71, No. 9 (1968), p. 1301). The mechanical energy is applied to the solid body by means of grinding, friction, sliding, cutting, centrifuging, impact, and the like.

Such a mechanochemical action can be easily applied to the materials, for example, when the materials are mixed and ground by a ball mill. A treatment using the ball mill can be performed at room temperature after water has been added to the mixture of raw materials. The grinding time is normally 5 to 48 hours.

Subsequently, the materials are subject to a solid-water system reaction. A solid-water system reaction is a reaction which utilizes the difference in water solubility of a raw material system and a product system. Since the solubility of the materials is higher than that of produced FAp, once FAp is produced, it does not dissolve again but precipitates. Therefore, a reaction equilibrium is always shifted to the product side and the FAp producing reaction progresses. Note that the temperature at which this reaction occurs is 100° C. or less and is preferably 80° to 100° C. With the conventional dry method, since fluorine evaporates during the reaction, the composition becomes more uniform. Generally, fluorine of fluorapatite begins to evaporate at about 400° C, and the rate of evaporation increases as the temperature increases. In the present invention, however, since the reaction can be performed at a low temperature, as described above, fluorine is not caused to evaporate during the reaction and the composition does not become ununiform. The reaction time of this solid-water system reaction is normally 8 to 12 hours. This solid-water system reaction is quantitative and does not substantially produce byproducts.

When the reaction is complete, FAp is recovered by means of filtration and the like, and it is then dried. The thus-obtained FAp is a fine powder which has a particle size of 0.1 to 0 4 $\mu$m as measured by a scanning electron microscope, and has a good crystallinity. FAp produced with this method has a good sintering property, and can, surprisingly, be sintered at a temperature as low as 700° to 800° C. so as to be suitable for a moisture sensitive resistor. This temperature which has been range is lower than the temperature required for sintering FAp which has been produced by the dry method (about 300° C.).

The moisture sensitive resistor of the present invention can be obtained by sintering the FAp powder which has been produced by the above method. When electrodes are provided to this moisture sensitive resistor, a moisture sensitive element having an excellent moisture sensitive characteristic can be fabricated.

FIG. 1 is a sectional view of moisture sensitive element 10 having moisture sensitive resistor 11 of the present invention. Element 10 has resistor 11 made of sintered FAp. Electrodes 12 and 13 are formed on the two surfaces of resistor 11 and connected to resistance measuring element 14. Measuring element 14 measures the resistance of sensitive element 10. It is noted that the resistance of sensitive element 10 corresponds to the relative humidity of the atmosphere, and thus the humidity of the atmosphere can be determined.

It is generally known that when FAp is sintered, fluorine evaporates at above 400° C., and FAp is caused to react with the atmospheric water moisture at the vacancies which have been occupied by the evaporated fluorine and is converted into hydroxyapatite. The higher the sintering temperature, the higher the degree of conversion. This conversion is undesirable since the logarithm of the resistance of hydroxyapatite is higher than that of FAp by about 1, as is apparent from the Examples described below. Therefore, it is not advantageous to introduce a hydroxyl group which causes the conversion into a moisture sensitive resistor, particularly when measurement in a low humidity range is to be performed. For these reasons, FAp which can be sintered at a lowest possible temperature is desired in manufacture a moisture sensitive resistor. However, FAp manufactured in accordance with the conventional method does not satisfy such a demand. In contrast to this, FAp manufactured in accordance with the method of the present invention has a good sintering property, as described above, and can be sintered at a temperature which is lower than that of FAp produced by conventional methods.

FAp constituting the moisture sensitive resistor according to the present invention can be represented by a formula $Ca_{10}(PO_4)_6F_2$. It is possible to substitute the calcium ions of the FAp within a range of 20 atom % or less by at least one type of cations having an ion radius of 0.95 Å (inclusive) to 1.35 Å (inclusive). These substituted FAp's can also be used as the material of the resister. Some of the substituted FAp's exhibit a lower resistance. Examples of such substituting cations include a monovalent cation such as sodium, potassium, copper, and silver; a divalent cation such as strontium, barium, titanium, chromium, manganese, cadmium, and lead; a trivalent cation such as indium, thallium, bismuth, and rare earth elements including, for example, scandium, yttrium, lanthanum and europium; and a tetravalent cation such as zirconium and hafnium. Fluorapatite substituted by any of the above cations can be obtained when calcium carbonate and calcium fluoride of the starting materials are partialy substituted by a source of the selected type of cations (e.g., a carbonate and oxide) and subjected to the same treatment as described above. When a carbonate is used as the cation source, the composition of the material is as follows:

| Cation for substitution | Composition of Material (molar ratio) |
| --- | --- |
| $M^+$ | $CaHPO_4:CaCO_3:CaF_2:M_2CO_3 =$ 6:3−X:1−X:X (0 < X ≦ 1) |
| $M^{2+}$ | $CaHPO_4:CaCO_3:CaF_2:MCO_3 =$ 6:3−X:1:X (0 < X ≦ 2) |
| $M^{3+}$ | $CaHPO_4:CaCO_3:CaF_2:M_2(CO_3)_3 =$ 6:3−X:1−X:X (0 < X ≦ 1) |
| $M^{4+}$ | $CaHPO_4:CaCO_3:CaF_2:M(CO_3)_2 =$ 6:3:1−X:X (0 < X ≦ 0.5) |

The present invention will be described by way of its Examples.

EXAMPLE 1

Figure 2:
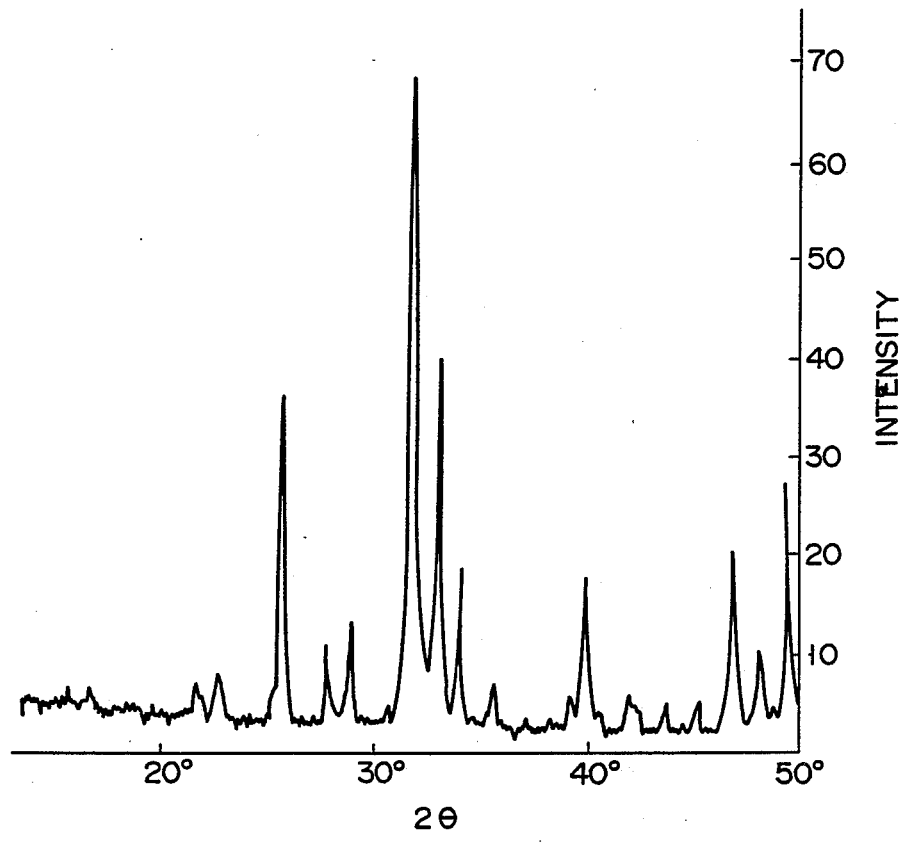
FIG. 2 is a graph showing an X ray diffraction pattern of FAp obtained by the method of the present invention.

Calcium monohydrogen phosphate, calcium carbonate, and calcium fluoride were weighed at a molar ratio of 6:3:1 such that the synthesized amount of FAp was 50 g. The materials were mixed and ground using a ball mill together with 200 ml of water for 24 hours at 80 rpm. The ground mixture was caused to react in water at 100° C. for 10 hours to obtain FAp. The obtained FAp was a fine powder having an average particle size of 0.2 $\mu$m as measured by a scanning electron microscope. FIG. 2 shows the X-ray diffraction pattern of this FAp.

EXAMPLE 2 polyvinyl alcohol was added to the FAp powder obtained in Example 1 and subjected to granulation.

The resultant granules were press molded to have a consolidated density of 1.5 g/cm$^3$, thus preparing a tablet having a diameter of 18.15 mm and a thickness of 1.0 mm. This tablet was sintered at 780° C. for 2 hours, thus obtaining a desired sintered body. Silver paste was coated on the two surfaces of the sintered body by screen process printing and the sintered body was baked at 530° C., thereby forming electrodes. A moisture sensitive element was thus obtained.

Figure 3:
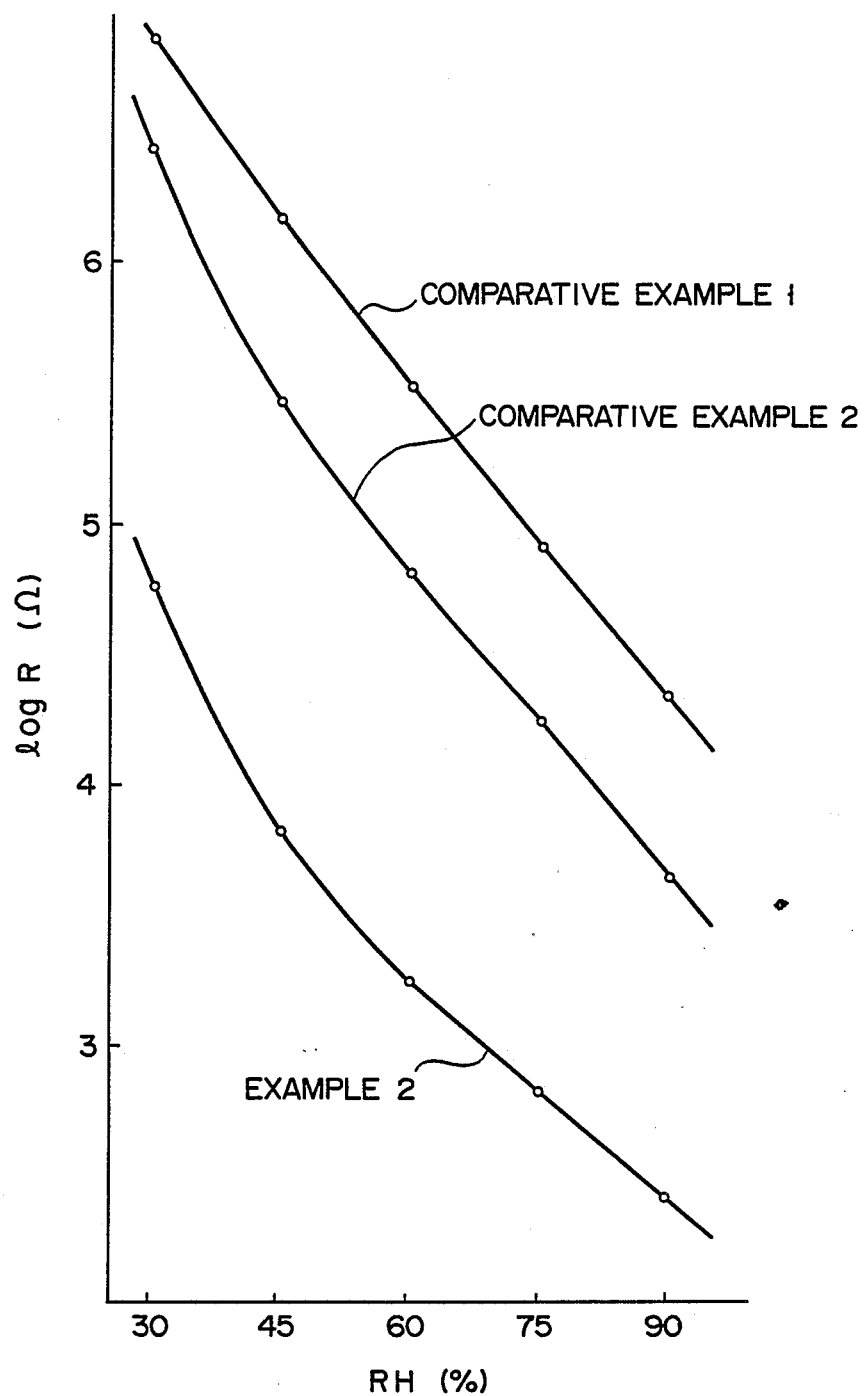
FIG. 3 is a graph showing the moisture sensitive characteristic of the moisture sensitive resistor fabricated using FAp exhibiting the X-ray diffraction pattern shown in FIG. 2 together with those of Comparative Examples.

The moisture sensitive characteristic (relationship between the logarithm of resistance [R] and relative humidity [RH]) of this moisture sensitive element is shown in FIG. 3. The measurement was conducted at 25° C., 1 kHz, and 1 V.

Figure 4:
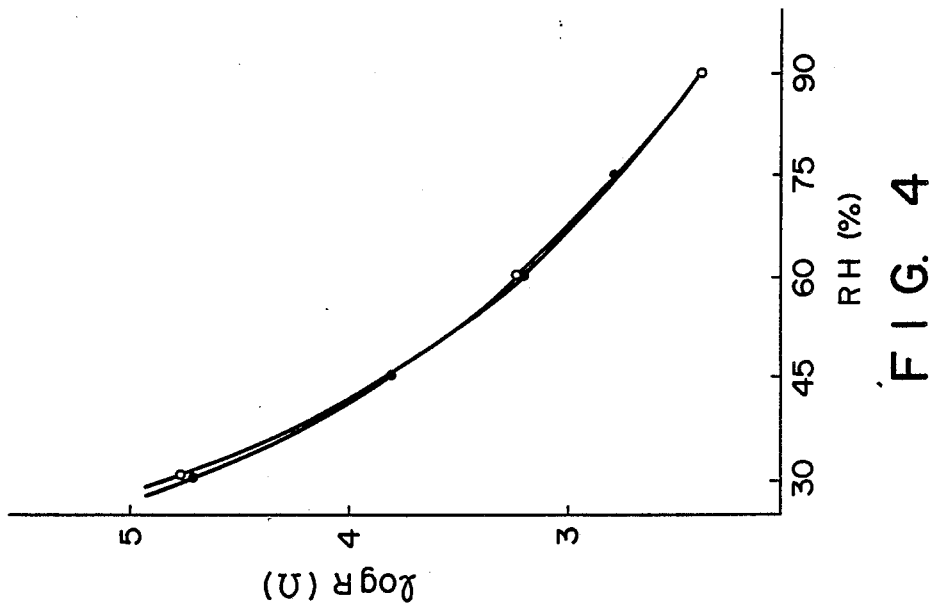
FIG. 4 is a graph showing the hysteresis of the resistance of the moisture sensitive element using the moisture sensitive resistor exhibiting the moisture sensitive characteristic shown in FIG. 3.

The resistance (R [$\Omega$]) of the moisture sensitive element made of sintered FAp obtained in this example was measured both when moistening was performed to increase a relative humidity (RH) from 30 to 90% and when dehumidification wa performed to decrease a relative humidity from 90 to 30%. The measurement was conducted at 25° C., 1 kHz, and 1 V. Table 1 (Process of Moistening) and Table 2 (Process of dehumidification) below show the measurement results. FIG. 4 shows a hysteresis curve obtained from the measurement results. Note that the resistance is indicated as a logarithm in FIG. 4.

TABLE 1

| | Process of Moistening | | | | |
|---|---|---|---|---|---|
| RH | 30% | 45% | 60% | 75% | 90% |
| R | 5.80 × 10$^4$ | 6.58 × 10$^3$ | 1.75 × 10$^3$ | 6.50 × 10$^2$ | 2.62 × 10$^2$ |

TABLE 2

| | Process of Dehumidification | | | | |
|---|---|---|---|---|---|
| RH | 90% | 75% | 60% | 45% | 30% |
| R | 2.62 × 10$^2$ | 6.69 × 10$^2$ | 1.69 × 10$^3$ | 6.61 × 10$^3$ | 5.34 × 10$^4$ |

COMPARATIVE EXAMPLE 1: FLUORAPATITE SYNTHESIZED BY A DRY METHOD

Herein, calcium monohydrogen phosphate, calcium carbonate, and ammonium fluoride were caused to react with one another by mixing them at a molar ratio of 6:4:1, placing them in a crucible which is open to the air, and heating at 950° C. for 4 hours to prepare FAp. A moisture sensitive element was then obtained by using the obtained FAp and following the same procedures as in Example 2, except that the consolidated density and sintering temperature were respectively set at 1.9 g/cm$^3$ and 1,200° C. The moisture sensitive characteristic of this element is shown in FIG. 3.

COMPARATIVE EXAMPLE 2: HYDROXYAPATITE

In this example the same operation was followed as in Example 1, except that calcium monohydrogen phosphate and calcium carbonate were weighed and mixed at a molar ratio of 6:4, and hydroxyapatite was obtained. A moisture sensitive element was obtained using the obtained hydroxyapatite and following the same operation as in Example 2 except that sintering was performed at 900° C. for 6 hours. The moisture sensitive characteristic of this element is shown in FIG. 3.

As is apparent from FIG. 3, the moisture sensitive resistor of the present invention has a lower resistance than moisture sensitive resistors which are made of sintered fluorapatite synthesized by the dry method or of sintered hydroxyapatite.

As is apparent from FIG. 4, hysteresis does not substantially occur in the resistance of the moisture sensitive resistor of the present invention.

EXAMPLE 3

Figure 5:
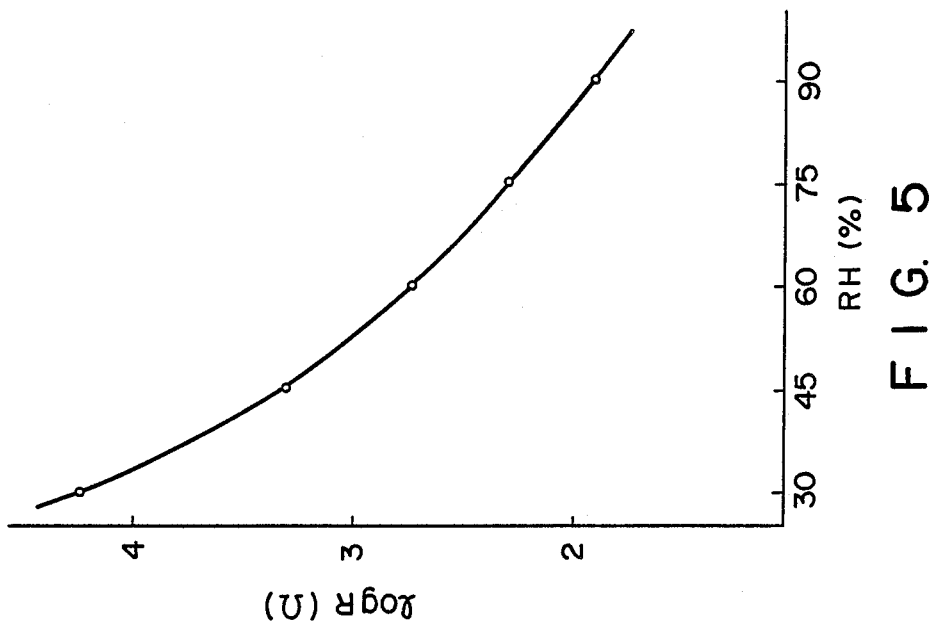
FIG. 5 is a graph showing the moisture sensitive characteristic of the moisture sensitive resistors according to another embodiments of the present invention.

Herein, calcium monohydrogen phosphate, calcium carbonate, calcium fluoride, and potassium carbonate were weighed at a molar ratio of CaHPO$_4$:CaCO$_3$:CaF$_2$: K$_2$CO$_3$ = 6:2.5:0.5:0.5. A moisture sensitive element was obtained using these powdery materials in accordance with the same method as used in Example 2. FIG. 5 shows the moisture sensitive characteristic of this element. The measurement conditions were 25° C., 1 kHz, and 1 V. This result shows that when FAp calcium ions are partially substituted by a predetermined type of cations, the resistance of the moisture sensitive element corresponding to the relative humidity is further decreased.

EXAMPLE 4

Figure 6:
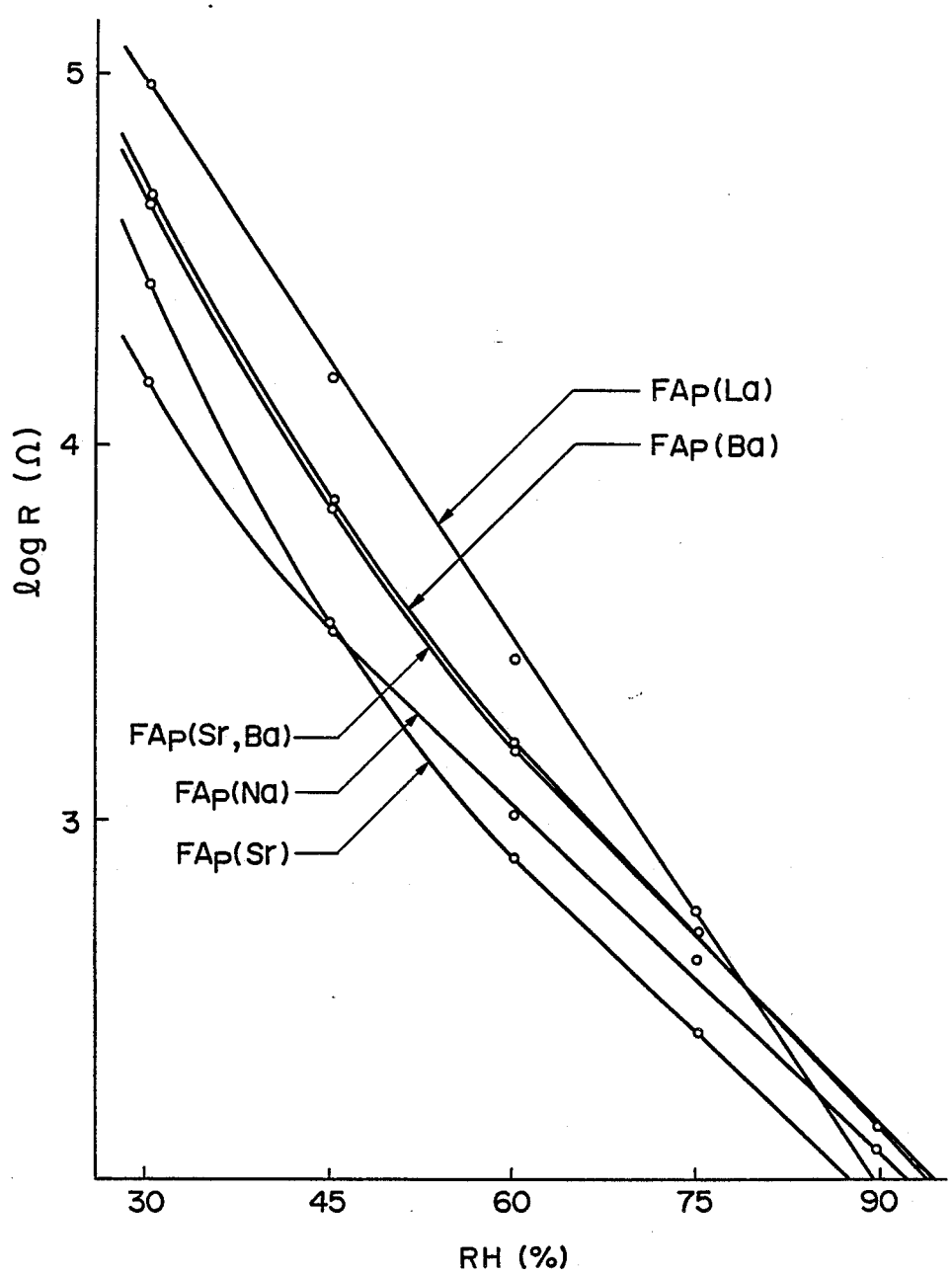
FIG. 6 is a graph showing the moisture sensitive characteristic of the moisture sensitive resistors according to still another embodiments of the present invention.

In this example the same operation as carried out in Example 2 was performed except that calcium monohydrogen phosphate, calcium carbonate, calcium fluoride, and sodium carbonate were used as the raw materials at a molar ratio of CaHPO$_4$:CaCO$_3$:CaF$_2$: Na$_2$CO$_3$ = 6:2.5:0.5:0.5, and that the sintering temperature was set at 900° C. The moisture sensitive characteristic of a moisture sensitive element made of a sintered body of the obtained Na-substituted FAp (FAp(Na)) is shown in FIG. 6.

EXAMPLE 5

In this example the same operation as used in Example 2 was performed except that calcium monohydrogen phosphate, calcium carbonate, calcium fluoride, and strontium carbonate were used as the raw materials at a molar ratio of CaHPO$_4$:CaCO$_3$:CaF$_2$:SrCO$_3$ = 6:2:1:1, and that the sintering temperature was set at 840° C. The moisture sensitive characteristic of a moisture sensitive element made of a sintered body of the obtained Sr-substituted FAp (FAp(Sr)) is shown in FIG. 6.

EXAMPLE 6

In this example the same operation as followed in Example 2 was performed except that calcium monohydrogen phosphate, calcium carbonate, calcium fluoride, and barium carbonate were used as the raw materials at a molar ratio of CaHPO$_4$:CaCO$_3$:CaF$_2$:BaCO$_3$ = 6:2:1:1. The moisture sensitive characteristic of a moisture sensitive element made of a sintered body of the obtained Ba-substituted FAp (FAp(Ba)) is shown in FIG. 6.

EXAMPLE 7

In this example the same operation as carried out in Example 2 was performed except that calcium monohydrogen phosphate, calcium carbonate, calcium fluoride, and lanthanum carbonate were used as the raw materials at a molar ratio of CaHPO$_4$:CaCO$_3$:CaF$_2$: La$_2$(CO$_3$)$_3$ = 6:2.5:0.5:0.5, and that the sintering temperature was set at 1,000° C. The moisture sensitive characteristic of a moisture sensitive element made of a sintered body of the obtained La-substituted FAp (FAp(La)) is shown in FIG. 6.

EXAMPLE 8

In this example the same operation as followed in Example 2 was performed except that calcium monohydrogen phosphate, calcium carbonate, calcium fluoride, strontium carbonate, and barium carbonate were used as the raw materials at a molar ratio of $CaHPO_4:CaCO_3:CaF_2:SrCO_3:BaCO_3 = 6:1:1:1:1$, and that the sintering temperature was set at 900° C. The moisture sensitive characteristic of a moisture sensitive element made of a sintered body of the obtained Sr, Ba-substituted FAp (FAp(Sr, Ba)) is shown in FIG. 6.

As described above, according to the present invention, an FAp having a uniform composition can be produced without substantially produce by-products.

The moisture sensitive resistor according to the present invention has a sufficiently low resistance corresponding to a humidity and substantially no hysteresis in the resistance.

What is claimed is:

1. A moisture sensitive resistor comprising a sintered body of fluorapatite prepared by a method comprising the steps of:
   (1) providing a mixture containing calcium monohydrogen phosphate, calcium carbonate, and calcium fluoride substantially in a ratio of $CaHPO_4:CaCO_3:CaF_2$ of about 6:3:1;
   (2) subjecting the mixture of a mechanochemical action selected from grinding, friction, sliding, cutting, centrifuging or impact;
   (3) reacting the mixture in water at a reaction temperature of at most 100° C. and thereby depositing fluorapatite from the reaction mixture as a precipitate; and
   (4) collecting the deposited fluorapatite from the mixture and forming same into a body.

2. The resistor produced by the process of claim 1, including the additional step (5) sintering the body at a temperature of 700° to 800° C.

3. A moisture sensitive resistor comprising a sintered body of fluorapatite prepared by a method comprising the steps of:
   (1) providing a mixture of calcium monohydrogen phosphate, calcium carbonate, calcium fluoride, and a metal carbonate in a ratio of:
      (a) $CaHPO_4:CaCO_3:CaF_2:M_2CO_3$ of about 6:3-X:1-X:X wherein M is sodium, potassium, copper, and silver, and $0 < X \leq 1$,
      (b) $CaHPO_4:CaCO_3:CaF_2:MCO_3$ of about 6:3-X:1:X wherein M is strontium, barium, titanium, chromium, manganese, cadmium, and lead, and $0 < X \leq 2$,
      (c) $CaHPO_4:CaCO_3:CaF_2:M_2(CO_3)_3$ of about 6:3-X:1-X: X wherein M is indium, thallium, bismuth, scandium, yttrium, lanthanum, and europium, and $0 < X \leq 1$,
      (d) $CaHPO_4:CaCO_3:CaF_2:M(CO_3)_2$ of about 6:3:1-X:X wherein M is zirconium and hafnium, and $0 < X \leq 0.5$, or
      (e) a mixture of any two or more of (a), (b), (c) and (d);
   (2) subjecting the mixture of step (1) to mechanochemical action selected from grinding, friction, sliding, cutting, centrifuging, or impact;
   (3) reacting the mixture in water at a reaction temperature of at most 100° C. and thereby depositing fluorapatite from the reaction mixture as a precipitate; and
   (4) collecting the deposited fluorapatite from the mixture and forming same into a body.

4. A resistor produced by the process of claim 3, wherein the metal ions of the metal carbonate are sodium, potassium, strontium, barium, or lanthanum.

* * * * *